United States Patent
Sethna et al.

(10) Patent No.: US 6,960,700 B1
(45) Date of Patent: Nov. 1, 2005

(54) ADSORBENT BEDS FOR REMOVAL OF HYDRIDES FROM HYDROCARBONS

(75) Inventors: Rustam H. Sethna, Palatine, IL (US); Jayant K. Gorawara, Buffalo Grove, IL (US); Henry Rastelli, Gurnee, IL (US); Daniel L. Ellig, Arlington Heights, IL (US); Vladislav I. Kanazirev, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/326,658

(22) Filed: Dec. 19, 2002

(51) Int. Cl.$^7$ ................................................ C07C 7/12
(52) U.S. Cl. ...................... 585/822; 585/823; 585/824; 585/809
(58) Field of Search ................... 585/822, 823, 585/824, 809

(56) References Cited

U.S. PATENT DOCUMENTS

| | | | |
|---|---|---|---|
| 3,782,076 A | 1/1974 | Carr et al. ..................... | 55/74 |
| 3,833,498 A | 9/1974 | Stahfeld ..................... | 208/307 |
| 4,744,221 A | 5/1988 | Knollmueller ................. | 62/48 |
| 4,861,939 A | 8/1989 | Debras et al. .............. | 585/820 |
| 4,957,715 A | 9/1990 | Grover et al. .............. | 423/228 |
| 5,302,771 A | 4/1994 | Venkatram et al. ......... | 585/823 |
| 5,330,560 A | 7/1994 | Chao et al. .................... | 95/95 |
| 5,704,965 A | 1/1998 | Tom et al. ..................... | 95/95 |
| 5,990,372 A | 11/1999 | Blankenship et al. ....... | 585/823 |
| 6,033,556 A | 3/2000 | Didillon et al. ............. | 208/253 |

*Primary Examiner*—Thuan D Dang
(74) *Attorney, Agent, or Firm*—John G. Tolomei; Mark Goldberg

(57) ABSTRACT

A process for removal of trace impurities of hydrides of arsenic, phosphorus, antimony, silicon, and boron and sulfur and oxygenates and compounds containing these impurities from a hydrocarbon stream comprising contacting the hydrocarbon stream with an adsorbent material selected from the group consisting of zeolites and promoted alumina to adsorb compounds containing sulfur and/or oxygenates, contacting the hydrocarbon stream with an adsorbent material comprising one or more active metal oxides to remove the hydrides and contacting the hydrocarbon stream with an adsorbent material that removes water.

4 Claims, No Drawings

ADSORBENT BEDS FOR REMOVAL OF HYDRIDES FROM HYDROCARBONS

BACKGROUND OF THE INVENTION

This invention relates to adsorbents for the removal of trace elements, usually present as hydrides, from hydrocarbon streams and a process for their use. More specifically, it relates to a multi-layer adsorbent bed for adsorbing hydrides of arsenic, phosphorus, antimony, boron, silicon, as well as certain sulfur compounds. This invention is particularly useful in the treatment of polymer grade propylene for the manufacture of polypropylene, but also is useful in purification of other hydrocarbon streams.

In addition to the well-known contaminants such as hydrogen sulfide, carbonyl sulfide and mercaptans, light olefin-containing hydrocarbon feedstocks often contain a small quantity of arsine. Usually arsine is present to the extent of only several hundred parts per billion (ppb) by weight. However, even this small amount is normally beyond the allowable limits of an acceptable product (typically less than 20 ppb). The presence of arsine, even at very low concentrations, reduces the polymer yield of olefin catalysts significantly. For example as disclosed in U.S. Pat. No. 4,861,939, at 20° C., 15 bar, WHSV of 6 kg/kg-hr, Ziegler-type catalyst when 305 ppb $ArH_3$ is present, the yield was 10,000 kg polypropylene per kilogram of catalyst, while when there was less than 3 ppb of $ArH_3$, the yield was 32,000 kg polypropylene per kilogram of catalyst. High purity olefins are required for the satisfactory production of many polymeric products, especially those useful as plastics, including polymers of ethylene and propylene. However, arsine is a powerful reducing agent, which appears able to reduce the olefin polymerization catalysts and cause their deactivation. As a result, there has been a real need for improved techniques for removing arsine from light olefin-containing hydrocarbons, especially those used for polymer production.

The purification of propylene and other olefin feed streams is particularly complicated by the small difference between the boiling points of propylene and arsine which hampers arsine removal by fractionation. Consequently, the levels of arsine impurity in propylene stocks are often intolerably high.

The hydrides of boron, silicon, arsenic, phosphorus and antimony are known to be severe catalyst poisons in a variety of processes, including the manufacture of polypropylene and polyethylene. There are other hydrides, including metal hydrides and organometallic hydrides that also act as catalyst poisons. The polymerization reactions to make polypropylene and polyethylene occur over high activity Ziegler-Natta type catalysts or the newly developed metallocene single site catalysts. In order to provide the best catalytic activity of these catalysts, the feed olefin and any other hydrocarbon streams, such as comonomer streams, must be free of contaminants that can bond to the transitional metal groups on the catalyst, thus deactivating the catalyst. The metallocenes are extremely sensitive to arsine and phosphine with sensitivity to levels in the parts per billion (ppb) level range. Most polypropylene manufacturers specify extremely low levels of arsine and phosphine contamination in their propylene supplies with specifications set anywhere from 5 to 50 ppb of either of these impurities. Even the traditional Ziegler-type catalysts, which are less sensitive to these impurities, will produce greatly increased yields upon the removal of the impurities from the propylene. The same issues are present in the manufacture of various other polymers, including polyethylene, polystyrene and various elastomers.

In addition to removal of arsine and phosphines, it is important to remove sulfur compounds. There have been extensive previous efforts to develop adsorbents for the purification of propylene and other hydrocarbons.

U.S. Pat. No. 3,782,076 discloses a process for reducing the arsenic content, believed to be present as arsine, from gaseous hydrocarbon streams by contacting said streams with supported lead oxide. However, the presence of sulfur compounds is said to interfere with the removal of arsine, and furthermore the supported lead oxide may not be regenerated when sulfur compounds are present in the feed.

U.S. Pat. No. 3,833,498 discloses a process for reducing the arsenic content, believed to be present as arsine, from gaseous hydrocarbon streams by contacting said streams with activated carbon derived from a bituminous coal and containing cobalt, nickel, molybdenum and vanadium. However, the feed should be substantially dry and free of sulfur compounds.

U.S. Pat. No. 5,330,560 discloses a process for recovery of arsenic from a gas, such as natural gas, using an inert solid support coated with phosphoric acid and a metal halide, such as ferric chloride or cupric chloride.

U.S. Pat. No. 5,302,771 describes the use of a modified alumina to remove impurities from liquid hydrocarbon streams, such as propylene. The alumina is impregnated with a metal selected from lithium, potassium, calcium, magnesium, barium and sodium.

U.S. Pat. No. 5,990,372 discloses an adsorbent for removal of trace amounts of sulfur, mercury, arsenic, metal hydrides and mixtures thereof, where the adsorbent is a combination of iron oxide, manganese oxide and a support material.

U.S. Pat. No. 6,033,556 discloses the use of a capture mass comprising an alumina support with a metal oxide or sulfide. Metals used included copper, molybdenum, tungsten, iron, nickel and cobalt. The capture masses were used to trap heavy metals, including arsenic, mercury and lead.

U.S. Pat. No. 4,744,221 discloses a method of storing and delivering arsine by contacting a zeolite having a pore size between 5 to 15 angstroms with arsine, at a temperature between −30° C. and 30° C. and then heating the arsine-adsorbed zeolite to a temperature not greater than 175° C. to release a portion of the arsine.

U.S. Pat. No. 5,704,965 discloses a fluid storage and delivery system using a carbon sorbent material that has an affinity for a variety of fluid reagents, including arsine and phosphine.

There still remains a need for improved materials to remove the arsine and phosphine from hydrocarbon streams as well as the sulfur impurities and oxygenates, especially in light of the intolerance of the new polymerization catalysts for these impurities. In particular, there remains a need to overcome the difficulty caused by sulfur compounds being adsorbed and limiting the capacity for the adsorbents to remove arsine and phosphines which, while present in much smaller concentrations than the sulfur compounds, must still be removed.

It is an objective of this invention to provide the simultaneous removal of sulfur compounds, arsine, phosphine and oxygenates, including water, methanol and carbon dioxide from propylene and other hydrocarbon streams.

SUMMARY OF THE INVENTION

In accordance with the present invention, there is provided a multi-layer adsorbent bed for purification of ethylene, propylene and other $C_2$ to $C_4$ hydrocarbons, comprising a guard layer of a sulfur removal adsorbent, at least one layer of adsorbent to remove hydrides including boron, silicon, arsenic, phosphorus, antimony and other hydrides. The arsenic hydrides are normally present in the highest concentrations. Oxygenates, including water, methanol and carbon dioxide are also removed within the multi-layer adsorbent bed. Water is a byproduct of the hydride removal and is also a contaminant that needs to be removed from the hydrocarbon stream. The sulfur and/or oxygenate removal layer is zeolite 13X or 5A or other appropriate adsorbent, the arsine/phosphine and other hydrides removal layer is a transition metal oxide on alumina and the water removal layer can be a variety of adsorbents, such as zeolite 3A. In one embodiment of the invention, the arsine/phosphine removal layer comprises CuO. In another embodiment, the arsine/phosphine removal layer comprises a highly dispersed CuO on alumina such that an X-ray of the CuO on alumina does show a considerably reduced CuO diffraction pattern compared to a typical CuO diffraction pattern.

The present invention is also a process for the removal of trace contaminants from a hydrocarbon stream including arsine, phosphine, sulfur compounds and oxygenates, comprising contacting the hydrocarbon stream with a multi-layer adsorbent bed comprising a sulfur compound and oxygenate removal bed, an arsine/phosphine removal layer and a water removal layer.

In another embodiment of the invention, the arsine/phosphine removal layer and the oxygenate removal layer are combined, either by an admixture of the two adsorbents or by use of a hybrid adsorbent. However, the sulfur removal layer needs to remain separate from the arsine/phosphine removal layer due to the tendency for the adsorption of the sulfur to block adsorption of arsine and phosphine and other hydrides. It is also contemplated within the scope of the present invention, that more than one adsorbent layer may be employed to remove hydrides.

In yet another embodiment of the invention, the sulfur removal layer and the oxygenate and water removal layer can be regenerated, while the arsine/phosphine removal layer, although non-regenerable, is subject to the regeneration conditions at which the other layers are regenerated. In one embodiment of the invention, a heated flow of gas first desorbs oxygenates, such as water from the oxygenate removal layer and then desorbs the sulfur and sulfur compounds from the sulfur removal layer. The full regeneration of the sulfur removal layer is enhanced by the use of this water containing gas. This regeneration can be completed by continued passage of a heated gas through these layers after removal of the water and other oxygenates has been essentially completed.

DETAILED DESCRIPTION OF THE INVENTION

The present invention relates to the removal of arsenic hydride, often referred to as arsine in its most frequently occurring form, from light olefin-containing hydrocarbon streams. It further relates to the removal of other hydrides, including phosphorus hydrides, antimony hydrides, silicon hydrides and boron hydrides. In addition, sulfur compounds and oxygenates are removed. The hydride removal process of the present invention reduces the arsine concentration in the treated hydrocarbon feedstock to 20 parts per billion by weight (ppb) and preferably 5–10 ppb or lower with similar reduction in the concentration of other hydrides that may be present in a hydrocarbon stream. The original arsine concentration in the feedstock may be as high as 1000 parts per million by weight (ppm) or higher depending on the process of manufacture, as well as depending upon the origin of the hydrocarbon feedstock.

The hydrocarbon feedstock is purified by passage through a multi-layer bed. There are a minimum of two beds, with one bed for the removal of sulfur and at least a second bed for the removal of hydrides as well as water. In the preferred embodiment of the invention the hydrocarbon will first pass through a layer for sulfur compound and oxygenate removal, comprising a layer of zeolites including various ion exchange forms, including transition metals, preferably zinc. The zeolites that can be used include faujasites (13X, CaX, NaY, CaY, ZnX), chabazites, clinoptilolites and LTA (4A, 5A) zeolites.

Another type of layer for sulfur compound and oxygenate removal that is effective in the practice of the present invention is a promoted alumina. The promoter is selected from one or more alkali metals or alkaline earth metals. The preferred alkali metals include sodium and potassium and the preferred alkaline earth metals include magnesium and calcium. The next layer is an adsorbent for arsine, phosphine, antimony hydride and other hydrides, also operating as a guard bed. The preferred materials for this hydride guard bed are active metal oxides which are broadly defined as including transition metal oxides, such as copper oxides and manganese oxide and other transition metal oxides as well as zinc oxide and lead oxide. Particularly favorable results were found with copper oxide.

In one embodiment of the invention, the copper oxide was well dispersed on an alumina support. At the highly dispersed levels of copper oxide employed herein, X-ray comparison of test samples did show a reduced intensity of the x-ray peaks for CuO while standard prior art compositions did show more intense doublet X-ray peaks at about 35.5 and 38.8 angle 2 theta. It was found that better copper dispersion leads to better utilization of the copper with more arsine adsorbed per unit weight adsorbent than would otherwise be found. Smaller adsorber vessels may then be used with lower costs for capital outlays.

Water is produced as a byproduct to the removal of the arsine and other hydrides and needs to be removed from the hydrocarbon feedstock as well. Other oxygenates, including methanol and carbon dioxide also need to be removed. While feedstock oxygenate removal can be accomplished in the same portion of the bed as compound sulfur removal, a bed of a water removing material is also provided at the effluent end, preferably a 3A type bed.

In another embodiment of the present invention, the function of the arsine/phosphine removal layer and the water removal layer may be combined into a single layer. This would be done either by using a mixture of the arsine/phosphine removal material and the oxygenate removal material or by use of a hybrid or composite type material. It would be a simpler operation with only two adsorbents required. A high surface area support for the arsine adsorbent may be used for the purpose of water removal. The arsine/phosphine removal layer then functions also as a water removal layer. Once water is produced by the hydride reaction with the metal component, the water is immediately scavenged by the support.

EXAMPLE 1

A series of adsorbents were prepared for testing their capacity to remove arsine from hydrocarbons. The composition of these samples is shown in Table 1. The subscripts on the chemical formulas have been omitted to simplify the explanation hereinafter, but should be readily understandable to those skilled in the art. A-201 and A-300 alumina are activated alumina products of UOP LLC of Des Plaines, Ill.

TABLE 1

| Sample Designation | Description |
| --- | --- |
| A | 19% PbO on alumina |
| B | 90% MnO on alumina |
| C | 35% CuO/35% NiO/17% ZnO on alumina |
| D | Zn-X 8 × 12 beads (16% as ZnO) |
| G | A-201 + 9% CuO – Sprayed $Cu(NO_3)_2$ |
| H | A-300 powder + 13.6% CuO powder mixing – water and sodium acetate |
| I | A-300 powder + 17.6% CuO – Sprayed $Cu(NO_3)_2$ |
| J | CuO + $MnO_2$ on alumina |
| K | NiO bonded with Attapulgite clay |
| L | Aldrich $MnO_2$ powder |

Samples A, B, C, D, J, K and L are commercially available materials familiar to those skilled in the art.

Sample G was prepared by placing in a pan one hundred grams of activated alumina A-201 7×12 mesh, produced by UOP, Des Plaines, Ill. The sample was rotated at about 100 rpm while being sprayed with a $Cu(NO_3)_2$ $2.5H_2O$ solution containing about 0.13 mass % Cu. The product was cured in a closed container and activated in an air-purged oven at 400–420° C. The activated product had a BET surface area of about 320 m²/g. In another sample, a more concentrated cupric nitrate solution (about 23%) was used. A longer rotation time was used in order to allow for some of the water to be evaporated while rotating.

In Sample H, 91.6 g of activated alumina powder marketed by UOP as A-300 and 13.1 g CuO powder were mixed for about 10 minutes with occasional stirring in the rotating pan described above. About 30 g of the powder mixture was then rolled into small particles while spraying with a 14% sodium acetate solution followed by thermal activation as described above.

In Sample I, forty grams activated alumina powder were rolled into small beads while being sprayed with a 49% $Cu(NO_3)_2$ solution. The sample was cured in a closed container overnight and activated for about 2.5 hours at 360° C. in an air purged oven.

EXAMPLE 2

The following measurements effectively screen the materials listed in Table 1 for capacity for adsorbing arsine and were made on McBain-Bakr adsorption apparatus. In this process, the weight of the empty sample container was measured. A 1.0-gram sample of adsorbent was loaded into this container. The air present in the system was evacuated and the sample activated at 250° C. overnight. The activated weight was measured to establish the activated sample weight. The adsorbate, as shown in the tables below, was introduced at the indicated pressure. Then the sample was allowed to reach equilibrium and the equilibrated weight of the sample was taken. Then the percentage of adsorbed arsine was measured based upon the percentage increase in weight of the sample.

TABLE 2

Arsine Adsorption Screening (low pressure - 7 torr $AsH_3$)

| Sample | Active Metal | Support | Active Metal Content (grams metal/ 100 grams adsorbent) | Arsine Loading (wt-%) | Mole Ratio (As/Me) |
| --- | --- | --- | --- | --- | --- |
| A | Pb | $Al_2O_3$ | 16.58 | 2.21 | 0.35 |
| B | Mn | $Al_2O_3$ | 59.32 | 0.20 | 0.00 |
| C | Cu, Ni, Zn | $Al_2O_3$ | 53.08 | 5.89 | 0.09 |
| D | Zn | Zeolite X | 12.97 | 0.59 | 0.04 |

TABLE 3

Arsine Adsorption Screening (low pressure - 6 torr $AsH_3$)

| Sample | Active Metal | Support | Active Metal Content (grams metal/ 100 grams adsorbent) | Arsine Loading (wt-%) | Mole Ratio (As/Me) |
| --- | --- | --- | --- | --- | --- |
| G | Cu | $Al_2O_3$ | 7.05 | 5.39 | 0.62 |
| H | Cu | $Al_2O_3$ | 10.23 | 0.33 | 0.03 |
| I | Cu | $Al_2O_3$ | 9.60 | 10.74 | 0.91 |
| J | Cu/Mn | Clay | 22.05 | 5.86 | 0.19 |
| K | Ni | $Al_2O_3$ | 43.14 | 1.33 | 0.02 |
| L | Mn | None | 62.74 | 8.86 | 0.10 |

X-rays of samples G, H and I showed the advantage of highly dispersed copper oxide as used in the preferred embodiments of the present invention. Sample H, which had poorly dispersed copper oxide, exhibited very defined peaks on x-ray diffraction while samples G and I which were very well dispersed showed barely detectable peaks. Samples G and I had much superior loading of arsine as compared to Sample H, showing the correlation with dispersion and effectiveness in adsorbing arsine.

What is claimed is:

1. A process for purification of a hydrocarbon stream containing arsine consisting essentially of contacting the hydrocarbon stream with an adsorbent material consisting of copper oxide dispersed upon alumina wherein said copper oxide is dispersed to an extent that x-ray spectra of said copper oxide alumina exhibits a reduced intensity of x-ray peaks for said copper oxide in proportion to the copper oxide dispersion and wherein said adsorbent material remove arsine from said hydrocarbon stream producing a purified hydrocarbon stream after contact with said copper oxide dispersed upon alumina.

2. The process of claim 1 wherein said hydrocarbon is an olefinic or paraffinic stream.

3. The process of claim 1 wherein said hydrocarbon is a $C_2$ to $C_4$ hydrocarbon.

4. The process of claim 1 wherein said hydrocarbon is ethylene or propylene.

* * * * *